Figure 1:
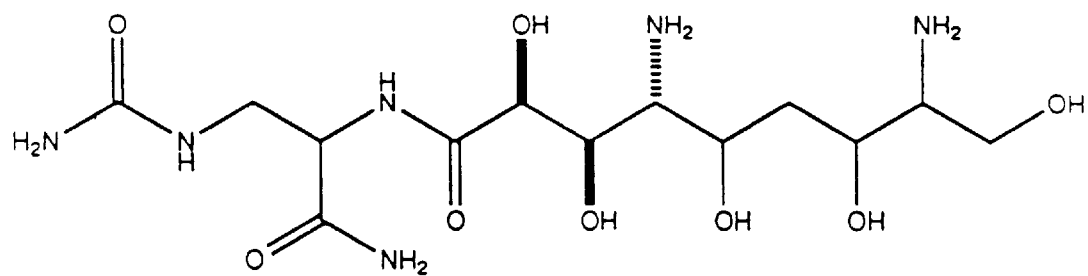

US006034124A

United States Patent [19]
Handelsman et al.

[11] Patent Number: 6,034,124
[45] Date of Patent: *Mar. 7, 2000

[54] FUNGICIDAL TOXINS FROM BIOCONTROL BACTERIA

[75] Inventors: Jo Handelsman, Madison; Laura Silo-Suh, Middleton, both of Wis.; Jon Clardy, Ithaca, N.Y.; Haiyin He, Chapel Hill, N.C.

[73] Assignee: Wisconsin Alumni Research Foundation, Madison, Wis.

[ * ] Notice: This patent is subject to a terminal disclaimer.

[21] Appl. No.: 09/212,554

[22] Filed: Dec. 16, 1998

Related U.S. Application Data

[63] Continuation of application No. 08/207,335, Mar. 8, 1994, Pat. No. 5,852,054, which is a continuation-in-part of application No. 07/878,800, May 5, 1992, abandoned, which is a continuation-in-part of application No. 07/758,644, Sep. 12, 1991, abandoned, which is a division of application No. 07/194,399, May 16, 1988, Pat. No. 5,049,379, which is a continuation-in-part of application No. 07/077,850, Jul. 27, 1987, abandoned, which is a continuation-in-part of application No. 06/890,402, Jul. 25, 1986, Pat. No. 4,877,738.

[51] Int. Cl.[7] .............................. A01N 47/28; C12N 1/20

[52] U.S. Cl. ......................... 514/488; 424/93.46; 564/59; 435/252.5

[58] Field of Search ......................... 514/488; 424/93.16; 435/252.5; 564/59

[56] References Cited

U.S. PATENT DOCUMENTS

| | | |
|---|---|---|
| 3,992,528 | 11/1976 | Graham . |
| 4,250,170 | 2/1981 | Kawaguchi et al. . |
| 4,259,317 | 3/1981 | Vesely et al. . |
| 4,877,738 | 10/1989 | Handelsman et al. . |
| 4,878,936 | 11/1989 | Handelsman et al. . |
| 5,049,379 | 9/1991 | Handelsman et al. . |

FOREIGN PATENT DOCUMENTS

| | | |
|---|---|---|
| 0193608 | 9/1986 | European Pat. Off. . |
| 0304178 | 2/1989 | European Pat. Off. . |
| WO8800966 | 2/1988 | WIPO . |

OTHER PUBLICATIONS

Buchanan et al, *Bergey's Manual of Determinative Bacteriology,* 8th Ed., pp. 532–535 (1974).

Gilbert et al., "Effects of an Introduced Bacterium on Bacterial Communities on Roots," *Ecology,* 74(3):840–854 (1993).

Gurusiddaiah, et al., "Characterization of an Antibiotic Produced by a Strain of *Pseudomonas Fluorescens* Inhibatory to Gaeumannomyces Graminisvar, tritici and Pythium spp.," *Antimicrobial Agents and Chemotherapy,* 29:3:488–495 (1986).

Halverson, et al., "Population Biology of *Bacillus cereus* UW85 in the rhizosphere of Field–Grown Soybeans," *Soil. Biol. Biochem.,* 25:485–493 (1993).

Halverson, et al., "Variable stability of antibiotic–resistance markers in *Bacillus cereus* UW85 in the soybean rhizosphere in the field," *Molecular Ecology,* 2:65–78 (1993).

Halverson, et al., "Enhancement of Soy Bean Nodulation by *Bacillus cereus* UW85 in the Field and a Growth Chamber," *Applied and Environmental Microbiology*, 57:9:2767–2770 (Sep. 1991).

Handelsman, "Abstract" on the Isolation of *Bacillus cereus* presented at a meeting on or after Jul. 26, 1986.

Handelsman, et al., "Zoospore Lysis Biocontrol of *Phytophthora megasperma* by *Bacillus cereus* UW85" Dept. Of Plant Pathology, University of Wisconsin, Madison, WI 53706 (Published Aug. 1987).

Handelsman, et al., "Biological Control of Damping–off of Alfalfa Seedlings With *Bacillus cereus* UW86," *Applied and Environmental Microbiology,* 56:713–718 (Mar. 1990).

Howell, et al., "Control of *Rhizoctonia solani* on Cotton Seedlings with *Pseudomonas florescens* and with Antibiotic Produced by the Bacterium," *Phytopathology,* 69:5:480–482 (1979).

Howell, et al., "Supression of *Pythium ultimum*–Induced Damping–Off of Cotton Seedlings by *Pseudomonas fluorescens* and Its Antibiotic Pyoluteorin," *Pytopathology,* 70:8:712–715 (1980).

Hutchins, A.S., "An In Vitro Inhibition of Root Rot Pathogens *Phellinus weiri, Armullariella mellea, Fomes annosus,* and *Phytophthora cinnamomi* by a Newly Isolated Bacillus sp., " *Microb. Ecol.,* 6(3):252–259 (1980).

Kamicker, et al., "Identification of *Baradyrhizobium Japonicum* Nodule Isolates From Wisconsin Soybean Farms," *Applied Environmental Microbiology,* 51:3:487–492 (1986).

Konishi, et al., "Cispentacin, A New Antifungal Antibiotic. 1. Production, Isolation, Physicochemical Properties and Structure," *Journal of Antibiotics,* 42:12:1749–1755 (1989).

Misaghi, et al., "Fungistatic Activity of Water–Soluble Fluorescent Pigments of Fluorescent Pseudomonads," *Phytopathology,* 72:1:33–35 (1982).

Oki et al., "Cispentacin, A New Antifungal Antibiotic," *The Journal of Antibiotics,* XLII:12:1756–62 (1989).

Pazinski, et al., "Influence of Azospirillum Strains on the Nodulation of Clovers by Rhizobium Strains," *Applied and Environmental Microbiology,* 49:4:984–989 (1985).

Smith, et al., "Suppression of Cottony Leak of Cucumber with *Bacillus cereus* Strain UW85," *Plant Disease,* Feb. 139–142 (1993).

Tschen, et al., "Bacereutin, an Antifungal Antibiotic Isolated from Metabolites of *Bacillus cereus* CHU 130," *Proceedings of the National Scientific Council B, Republic of China,* 13:4:258–261 (1989).

Wakayama, et al., "Mycocerein, A Novel Antifungal Peptide Antibiotic Produced by *Bacillus cereus,*" *Antimicrobial Agents Chemotherapy,* 26:6:939–940 (1984).

Yahalom, et al., Azospirillum Effects on Susceptibility to Rhizobium Nodulation and on Nitrogen Fixation of Several Forage Legumes, *Can. J. Microbiol,* 33:510–514.

*Primary Examiner*—Irene Marx

*Attorney, Agent, or Firm*—Quarles & Brady LLP

[57] ABSTRACT

A biocontrol bacteria, *Bacillus cereus* ATCC 53522, has been found to naturally synthesize two antibiotics, here designated zwittermicin A and antibiotic B. Zwittermicin A is a 396 dalton linear aminopolyol, a class of metabolite previously unknown in *B. cereus.* Antibiotic B is an aminoglycoside. Both antibiotics exhibit inhibitory activity on many fungal and bacterial pathogens.

1 Claim, 1 Drawing Sheet

FUNGICIDAL TOXINS FROM BIOCONTROL BACTERIA

CROSS-REFERENCE TO RELATED APPLICATIONS

This application is a continuation of application Ser. No. 08/207,335 filed Mar. 8, 1994, now U.S. Pat. No. 5,852,054, which was a continuation-in-part of application Ser. No. 07/878,800 filed May 5, 1992 abandoned, which was a continuation-in-part of Ser. No. 07/758,644 filed Sep. 12, 1991 abandoned, which was a divisional of Ser. No. 07/194,399 filed May 16, 1988 which issued on Sep. 17, 1991 as U.S. Pat. No. 5,049,379, which was a continuation-in-part of Ser. No. 07/077,850 filed Jul. 27, 1987 abandoned, which was a continuation-in-part of Ser. No. 06/890,402 filed Jul. 25, 1986 which issued on Oct. 31, 1989 as U.S. Pat. No. 4,877,738.

STATEMENT REGARDING FEDERALLY SPONSORED RESEARCH OR DEVELOPMENT

This invention was made with United States government support awarded by the following agencies:

AID, Grant No.: DHR-5600-G-00-0100-00
NSF, Grant Nos.: DCB8819401; DUE-9156087
USDA, AGRICCREE 92-34103-7170; AGRICCSRS 89-37262-4746; 593-0038-04;
USDA, Grant No: 89-34190-4316;
USDA, Grant No: 92-34190-6941;
The United States has certain rights in this invention.

TECHNICAL FIELD

The present invention relates to fungicidal compounds derived from biocontrol bacteria originally found useful in combatting damping off and root rots in plants.

BACKGROUND OF ART

Certain plants, of which alfalfa, soybeans, and common beans are examples, suffer from disease conditions called "damping off" and "root rot." The symptoms of damping off include the desiccation and subsequent death of seedlings soon after germination. Root rot symptoms include chlorosis and wilt of leaves and yellow to brown lesions with diffuse margins on roots and stems. The lesions can eventually lead to girdling and subsequent root decay resulting in decreased robustness in the plant or even in death. Often plants suffering from root rot begin by showing such symptoms, which may be mistaken as symptoms of drought and starvation. Such plants may be more vulnerable than healthy plants to attack by other pathogens, which are then mistaken as the cause of the death of the plants.

Damping off and root rot are merely two different sets of symptoms caused by infection of the plant by the same fungi and, in particular, by members of the Phytophthora, Pythium, Aphanomvces, Rhizoctonia, and Fusarium genera. Thus, *Phytophthora megasperma* f. sp. *medicaginis* (now formally known as *Phytophthora medicaginis*, and referred to hereinafter as "Pmm") causes both damping off and root rot in alfalfa when soils are wet in most parts of the world where alfalfa is grown, and *Phytophthora megasperma* f.-sp. *glycinea* has been shown to cause root rot in soybeans under wet growing conditions. However, fungi from among the other genera listed also are believed to attack alfalfa and soybeans. Root rot in common beans is believed caused by a complex of fungi including members of more than one of the genera referred to.

In general, control of damping off and root rot has been attempted by breeding for resistant plants. However, completely resistant cultivars have not been developed such that damping off and root rot remain major causes of crop loss. This is especially true under chronically wet growing conditions or when the same crop is planted repeatedly in the same fields. Certain fungicides such as metalaxyl partially control root rot. However, such fungicides are fairly expensive. For some crops, such as alfalfa, their use is not economically feasible. Also, resistance of the fungi to the fungicides can develop rapidly.

"Biological control" is defined as pathogen control by the use of a second organism. Mechanisms of biological control are diverse. For example, certain enteric bacteria have been examined for their usefulness in biological control of root rot in alfalfa. It is believed that control is obtained by competition between the enteric bacteria and the fungi for space on the surface of the alfalfa roots. In contrast, a toxin produced by one species of bacteria may be used to control another species of bacteria that appears as a pathogen. Bacterially produced antibiotics are an example of such toxins. The toxin can be isolated from the species producing it and administered directly, as is the common procedure with penicillin, or the species itself m ay be administered under appropriate circumstances to produce the toxin in situ. Once identified, such toxins produced by soil-dwelling bacteria may have utility in diverse other areas as antifungal or antibiotic agents.

BRIEF SUMMARY OF THE INVENTION

The present invention-is summarized in that an antibiotic toxin has been isolated from *Bacillus cereus*, the toxin being designated zwittermicin A, which is characterized and identified below.

The present invention is further summarized in the identification of a second toxin, here designed antibiotic B, al so isolated from *Bacillus cereus* and also characterized and identified below.

The present invention is also directed toward the use of the novel antibiotic, zwittermicin A, and antibiotic B toward the control of fungicidal and bactericidal disease.

Other objects, features and advantages of the present invention will become apparent from the following specification.

BRIEF DESCRIPTION OF THE DRAWING FIGURE

FIG. 1 illustrates the determined chemical structure of the zwittermicin A molecule.

DETAILED DESCRIPTION OF THE PREFERRED EMBODIMENT

An original bacterial strain was isolated from soil that exerts biological control over species of fungi responsible for damping of f and root rot in plants. The strain has been deposited in t he American Type Culture Collection, given the designation ATCC 53522, and shall hereinafter be referred to as "ATCC 53522." It has further been discovered that certain mutants of ATCC 53522 also provide biological control comparable to that provided by ATCC 53522. These bacteria have been obtained in substantially pure cultures. A "substantially pure" culture shall be deemed a culture of a bacteria containing no other bacterial species in quantities sufficient to interfere with replication of the culture. In addition, it has been discovered that the biological control is exerted by means of a toxin produced by the disclosed bacterial strains.

ATCC 53522 and what are defined below as its "protecting" mutants, together with antibiotics produced thereby, inocula containing the bacteria or their antibiotics, and methods for protecting plants from damping off and root rot that utilize the bacteria or their toxins are the subject of a co-pending patent application. Now a particular molecule, compounds found in supernatant fluid and other bacteria-free fluid and culture medium removed from a culture of ATCC 53522 or of its protecting mutants, has been found to be a "protecting antibiotic," as that term is defined below. These compounds have been so characterized as to be identifiable independent of its source in cultures of ATCC 53522, or its protecting mutants and, the two compounds shall be referred to herein by the coined terms "zwittermicin A" and "antibiotic B." Another fraction from the supernatant fluid from a culture of B. cereus ATCC 53522 has been found biologically active, having a capability to lyse Pmm zoospores, but, as revealed below, this zoolysin active fraction does not have the antifungal activity of the antibiotics.

The method by which the biological control referred to in the preceding paragraph may be verified to exist is the "plant protection assay" detailed below. "Biological control" of fungi causing damping off and root rot shall be deemed to exist if, when an effective quantity of ATCC 53522, its mutants that exhibit biological control, the antifungal toxin produced by them, Bacillus cereus antibiotic, or any other compound or molecule is placed in the soil or other growing medium in the immediate vicinity of the plant to be protected, a statistically significant reduction in the symptoms of damping off or root rot occurs. An "effective quantity" to combat damping off and root rot shall be that quantity sufficient to result in such a visibly significant reduction of symptoms. Clearly, if no quantity of a bacteria or any toxin or other compound is an effective quantity as so defined, that bacteria, toxin, or compound is not capable of exerting biological control over the fungi causing damping off and root rot.

ATCC 53522 and those of its mutants capable of exerting such biological control shall sometimes be referred to collectively as "protecting" bacteria. Bacillus cereus antibiotic and other toxins capable of exerting such biological control shall sometimes be referred to as"protecting" compounds or toxins. Plants, including seeds, seedlings, and mature plants, treated with such an effective quantity of protecting bacteria, their toxins, or Bacillus cereus antibiotic shall be referred to as "protected" from root rot or damping off.

ATCC 53522 was one of some 500 bacteria strains isolated from alfalfa roots and accompanying soil obtained from fields at the University of Wisconsin Experimental Farms at Arlington and Marshfield, Wis., and from two private farms at Verona and Cross Plains, Wis. The roots were cut into 1 cm segments, and each segment was placed in 10 ml of sterile, distilled water. The root segment and water then were sonicated at 20% maximum power with a Vibra-Cell 250 watt sonicator obtained from Sonics and Materials, Inc., Danbury, Conn. Sonication then was continued for 15 seconds. The sonicated mixture then was diluted in sterile, distilled water, and the dilutions were placed on trypticase soy agar (hereinafter referred to as "TSA") in petri plates to form dilution plates. TSA contains 30 g/l trypticase soy broth (hereinafter referred to as "TSB") obtained from BBL Microbiology Systems, Inc., Cockeysville, Md., and 15 g/l agar. TSA and TSB are conventional bacterial culture media well known to those skilled in the art.

The dilution plates were incubated at 28° C. for two days. For each root sample, bacterial colonies were selected from the dilution plate that had the highest number of distinguishable colonies. One colony of each visually distinguishable morphology on the plate was sampled with a sterile loop and was plated on a new TSA culture plate to allow the development of colonies in plates free from contamination by other bacteria. After two days incubation at 28° C., a single colony was selected from the resulting bacterial growth and was used to inoculate a TSA slant. The resulting slant cultures were stored at 4° C. until they were screened by the plant protection assay disclosed below.

Five hundred different slant cultures were obtained by this method. As a consequence of the isolation procedure just reviewed, it was extremely unlikely that any of these 500 cultures were immediate siblings. However, fewer than 500 separate bacterial species were isolated. For example, a number of different cultures were obtained of bacteria whose colonies had the appearance of Bacillus cereus, including the culture identified above as ATCC 53522. However, each of these cultures had been obtained from a different root segment, and the root segments themselves were obtained from fields from four different geographical locations. Consequently, the chances that a single strain was present in more than one slant culture are very small. This fact is confirmed by the appearance of ATCC 53522 in only one of the 500 cultures.

Each of the cultured isolates that were obtained by the procedure just described were screened for their ability to protect alfalfa seedlings from damping off caused by Pmm. Initial screening was performed on the cultivar Iroquois, which is known to be vulnerable to Pmm. One gram of Iroquois alfalfa seeds was soaked in 18 M sulfuric acid for 10 minutes. The seeds were then washed in 2 liters of sterile distilled water and were placed in 10 ml of sterile water and shaken at 28° C. for 24 hours. Next the seed coats were removed manually with forceps, and the seedlings were planted in test tubes containing 5 ml sterile, moist vermiculite. Three seedlings were planted in each test tube. Two days after the seedlings were planted, each test tube was inoculated with 0.3 ml of a three-day-old culture of the bacterial isolate to be tested. These cultures had been grown to saturation in TSB and had sporulated. Then each tube immediately was inoculated with $10^3$ zoospores of Pmm.

The Pmm zoospores had been produced by the method of S. A. Miller (1982) "Cytological and Biochemical Factors Involved in the Susceptible, Host Resistant and Non-host Resistant Interactions of Alfalfa with Phytophthora megasperma," Ph.D. thesis, University of Wisconsin. By this method, a sample of a colony of Pmm was transferred to an agar media on which it could grow. Conventional V8 media was used, consisting of 200 ml V8 vegetable juice, 2.5 g $CaCO_3$, and 15 g agar in 800 ml water. However, any agar media such as conventional tomato juice agar or carrot agar encouraging the growth of the fungus would be sufficient. The sample of the fungus colony was incubated at 24° C. for 4 days and then at 28° C. for an additional 3 days. A growing colony of Pmm developed. The agar around the colony was excised to leave a section of undisturbed agar with the growing fungus on it surrounded by a "moat" formed by the excision of agar. This moat was filled with sterile water to the level of the agar that had not been excised. The plate was incubated at 16° C. for one hour, whereupon the water was replaced, and the plate was incubated at 16° C. for an additional 5 hours. Zoospores were released from the fungus into the water of the moat. The concentration of zoospores in the water was measured with a hemacytometer, and a sample of the water was diluted with additional sterile water at 16° C. to reach a final concentration of zoospores of $10^4$/ml.

After addition of the zoospores, the test tubes containing the plants were incubated at 24° C. with a 12 hour photoperiod for 5 days, at which time the plants were evaluated for symptoms of damping off. Using Pmm and cultivar Iroquois, all control plants consistently were dead. Thus, the fact that a plant survived at all was evidence of biological control exerted by the bacterial isolate used. All bacteria that demonstrated that minimal amount of effectiveness for biological control were retested by this same method to verify the consistency of such control. The screening procedure just described constitutes a particular example of the plant protection assay described more generally below.

Of the 500 isolates from the 4 sites in Wisconsin referred to above, only ATCC 53522 strain was identified as having the ability consistently to exert biological control of Pmm in Iroquois alfalfa, as evidenced by at least 20 separate experiments. The level of control was such that alfalfa seedlings subjected to such control under the conditions of the screening procedure were visually indistinguishable from alfalfa seedlings that had never been exposed to Pmm. ATCC 53522 has been classified as *Bacillus cereus*, based on physiological tests, its colony morphology, and its spore size, shape, and position. Thus, ATCC 53522 produces acetoin, forms an acid from glucose broth, hydrolyzes starch, and grows in anaerobic agar. These characteristics, together with colony morphology, and spores size, shape, and position observed in ATCC 53522 are cited as distinctively characteristic of *Bacillus cereus* by R. E. Buchanan and N. E. Gibons, co-editors (1974), *Bergey's Manual of Determinative Bacteriology,* 8th Edition, pp. 532–535.

*Bacillus cereus* is a not uncommon bacterium in field soils. However, strains of *Bacillus cereus* demonstrating antifungal activity are almost unheard of. The inventors originally tested two known strains of *Bacillus cereus* obtained from entirely separate sources and found neither of them to exhibit the anti-fungal properties of ATCC 53522. Subsequently, as discussed further below, a method was derived to screen other field isolates for antibiotic production, and other such strains can now readily be found. In the original screening, however, of the 500 root-associated bacteria reviewed in the isolation process, many were probably *Bacillus cereus* and, in fact, many of them had the same colony morphology as ATCC 53522, but none of these other strains exhibited the antifungal qualities of ATCC 53522. S. Wakavama, et al. (1984), *Antimicrob. Agents Chemother.,* 26, 939–940, describe antifungal activity in a strain of *Bacillus cereus*. However, most of the antifungal antibiotics are made by *Bacillus subtilis*, which is easily distinguishable from ATCC 53522. The antifungal toxin produced by ATCC 53522 differs from that of the reported strain of *Bacillus cereus* referred to in that the toxin is of lower molecular weight and has different solubility properties. In addition, ATCC 53522 differs from the reported *Bacillus cereus* strain in that it grows anaerobically whereas the reported strain does not. Consequently, it is clear that the two *Bacillus cereus* strains are not the same and that their toxins are not the same.

The following is a disclosure of the plant protection assay whereby a test material such as a bacteria, an antibiotic, or the like, may be tested for its ability to exert biological control over a fungus capable of causing the symptoms of damping off or root rot. The seed of the plant to be protected is planted in a planting medium in the presence of damping off or root rot causing fungi. The planting medium may be a damp soil containing such fungi, vermiculite in water with the fungi present either in the vermiculite and water or in or on the seed, or any other planting medium in which the seed will grow and the fungi may freely develop. The bacteria, antibiotic, or other test material is placed at least in the immediate vicinity of the seed. Such placement shall be understood to be in the "immediate vicinity" of the seed if any soluble test material or any soluble exudate of a bacteria being tested will be in actual contact with the seed as it germinates.

Preferably the seed is coated with the test material, and when the test material is so used with respect to a seed, it shall be referred to hereinafter as a "seed inoculum." The process of coating seed with a seed inoculum is generally well known to those skilled in the art, and any conventional method that does not require conditions sufficiently harsh to kill bacteria or destroy toxins or other materials included in the seed inoculum is adequate. The plant seed to be protected is drenched in a broth culture of the bacteria and is mixed vigorously with it to coat the surface of the seed with the bacterial suspension. The seed may then be dried aseptically, preferably by being placed within a laminar flow hood on a sterile surface such as a sterile petri plate. The result is a dry, seed inoculum-coated seed. When the coated seed is planted in the planting medium, the test material accompanies it to reside in the immediate vicinity of the seed.

After a time sufficient for seedling growth and the expression of the symptoms of damping off, seedlings developing from the planted seed may be evaluated for visual evidence of protection, when compared to controls. In strains of alfalfa, known to be vulnerable to damping off, 2 weeks of growing time in a growth chamber at 24° C. with a 12 hour photoperiod was found to be a period sufficient for the expression of symptoms of damping off when seedlings were being grown in test tubes containing roughly $10^3$ to $10^4$ zoospores of Pmm or comparable, damping off-causing fungi. Protected seeds developed into seedlings visually indistinguishable from uninfected seeds while control seedlings developing from unprotected seeds were killed.

Protecting mutants of ATCC 53522 include both naturally occurring and artificially induced mutants. For example, ATCC 53522 is generally sensitive to the antibiotics rifampicin and neomycin. However, naturally occurring mutants of ATCC 53522 were isolated that exhibited resistance to one or the other of these antibiotics. Certain of these mutants, as well as one naturally occurring mutant distinguishable from the parent ATCC 53522 strain by the appearance of its colonies, are discussed in the Examples below and were found to protect alfalfa plants in the plant protection assay. Other mutants of ATCC 53522 were artificially induced by subjecting ATCC 53522 to the mutagen N-methyl-nitrogoguanidine in conventional ways, as is discussed in the Examples below. Most of these induced mutants also were found to protect alfalfa plants in the plant protection assay.

Various mutagenesis studies have also been done on cultures of ATCC 53522 which have resulted in mutant colonies which are deficient in production of the antibiotics and which are deficient in biocontrol activity, as determined by the biocontrol assays described herein. Those mutant colonies also were deficient in antibiotic production. An analysis of the mutant colonies for both biocontrol activity and for antibiotic accumulation revealed that the interpretation that the biocontrol activity was associated with the accumulation of both antibiotics as zwittermicin A and antibiotic B was consistent with the data uncovered from the mutant strains. Residual disease suppressive activity was detected in some strains that lack detectible antibiotic production, and such suppressive activity may be due to the zoospore-lysis activity or to another agent. This observation is consistent with the fact that many biocontrol bacterial colonies may depend on multiple strategies for disease suppression and the data would thus suggest that the antibiotics are required, but not sufficient, for the full biological control of cultures. Nevertheless, the antibiotics may have independent utility in other environments for the control of bacterial or fungicidal agents, as described in more detail below.

As has been disclosed above, it has been further discovered that active anti-root rot toxins, identified herein as the *B. cereus* antibiotics zwittermicin A and antibiotic B, are produced by ATCC 53522 and those of its mutants that are characterized by their abilities to protect plants from root rot in the plant protection assay. The two *Bacillus cereus* antibiotics may be collected from growth media in which the bacteria have been cultured and has been prepared in a substantially pure form. A preparation of *Bacillus cereus* antibiotic shall be deemed "substantially pure" if it is sufficiently free of interfering substances as to be able to be active to inhibit root rot by Pmm. The two *Bacillus cereus* antibiotics are effective to protect plants from damping off and root rot, even when separated from the bacteria producing it and applied to seed and to seedlings that have been placed in a planting medium containing root rot causing fungi. As is discussed below, the effectiveness of the application of two *Bacillus cereus* antibiotics is demonstrable by the plant protection assay, with the antibiotic being substituted for a protecting bacteria. Thus, the invention includes either or both antibiotics and a seed inoculum containing effective quantities of either *Bacillus cereus* antibiotic.

As has been disclosed above, the *Bacillus cereus* antibiotics may be isolated from ATCC 53522 and its protecting mutants by filtering the bacteria from the culture media in which they have been grown to a sporulated culture. Other conventional purification and concentration steps may then be undertaken as may be considered convenient or desirable, so long as the toxin remains active, as may be demonstrated by the plant protection assay.

Both of the antibiotics from *Bacillus cereus* described herein can be readily isolated from cultures of *Bacillus cereus* ATCC 53522 by culture of the bacteria and concentration of the resulting antibiotics from the culture supernatant. The supernatant can be fractionated in a column and then separated by electrophoresis to identify fractions which exhibit the biocontrol activity. It has been found that both antibiotics will stain with ninhydrin or silver nitrate.

The chemical formula and structure of the antibiotic zwittermicin A has been studied extensively. The molecular weight of a molecule, which was originally identified as *Bacillus cereus* antibiotic, was originally thought to be between 500 and 1000 daltons. Subsequent measurement of the molecular weight of purified antibiotic, now referred to a zwittermicin A, by mass spectroscopy revealed a molecular weight of about 396 daltons. The zwittermicin A antibiotic is soluble in methanol and insoluble in acetone, chloroform, and ethyl acetate. The antibiotic zwittermicin A moves as both an anion and a cation in an electric field, although it is a very weak anion. In repeated experiments, the antibiotic zwittermicin A has been tested for various protecting abilities by plant protection assays. The tests, some of which are discussed below, have revealed that the zwittermicin A antibiotic has proven useful antibiotic capabilities against Phytophthora and Pythium species as well as other fungal species. In addition, the antibiotic zwittermicin A also inhibits growth of some bacteria, notably *Erwinia herbicola*, several Pseudomonas species, and some *E. coli* strains.

The chemical structure for the zwittermicin A molecule has been tentatively identified. Shown herewith in FIG. 1 is the determined chemical structure of the molecule which has been identified. The molecule is an aminopolyol antibiotic which represents a new class of antibiotics isolated from Bacillus species. Zwittermicin A is a very weak acid, and will migrate as an anion at pH 9.2 as did other amide-containing compounds. It is appropriate to rely on biological activity as a detection method during purification or fractionation because the antibiotic zwittermicin A does not contain chromophores that can be detected spectrophotometrically.

Structure illustrated on FIG. 1 was determined by NMR and mass spectrometry studies of the native molecule, the acetylated derivative, and a hydrolysis product. While it is believed that this structure is correct, it is yet possible that there might be minor misplacements of smaller residues without affecting the overall chemical characterization or structure of the molecule. It is known, as described above, that the molecule is certainly a linear aminopolyol, a cation, and a very weak acid. The structure disclosed in FIG. 1 is consistent with that interpretation and is believed to be the correct molecular structure.

At this point, an incomplete structure is known for the antibiotic B. The antibiotic B also shows inhibitory activity in a biocontrol assay. The antibiotic B will also bind to CM-sephadex or amberlight IRC-50 at pH 7.0 and will elute when the pH is raised above 10.0. The staining properties and nuclear magnetic resonance profile of antibiotic B indicates that it is an aminoglycoside. While the antibiotic B has a slightly narrower spectrum of antifungal and antibacterial activity than zwittermicin A it nevertheless exhibits reasonably broad antifungal and antibacterial efficacy.

As the examples below indicate, both zwittermicin A and antibiotic B have significant activity against a variety of pathogenic fungi and bacteria. As the data also indicate, not only are the antibiotics useful separately, they also have certain synergistic activities when used in combination with each other. It is believed that the antibiotics can be prepared by culture of the *Bacillus cereus* ATCC 53522, but can equally be recovered from a wide variety of other *Bacillus cereus* cultures. Described below is a plant protection assay developed to test plant protection activity as initially isolated using ATCC 53522. It is believed that that same assay can be used to test other candidate *Bacillus cereus* strains for biocontrol activity and it is believed that those strains would also make one or both of the antibiotic zwittermicin A or antibiotic B described herein.

The antibiotics may readily be isolated from colonies of bacteria which produce them, such as ATCC 53522 by recovering the supernatant from sporulating colonies of the microorganisms. The supernatant, as described above, can be fractionated in a column and then separated by electrophoresis to identify the fractions which exhibit the biocontrol activity. Using high voltage paper electrophoresis, the two molecules identified herein as zwittermicin A and antibiotic B can readily be repeatably recovered. At pH 9.2, the high voltage paper electrophoresis (HVPE) yields 2 spots which are associated with biocontrol activity. The first spot, associate with zwittermicin A, had a relative mobility ($R_f$) of 0.30 compared with orange G. The antibiotic B spot had an $R_f$ of 0.032. If the same HVPE process is conducted at pH 1.7, the relative mobilities of zwittermicin A and antibiotic B are $R_f$-1.042 and −0.909 respectively.

As described below, both zwittermicin A and antibiotic B have a broad antibiotic activity against many fungal, and also some bacterial, pathogens. The activity extends not only to plant pathogens, but also to potential mammalian pathogens. It is also revealed from the data below, the level of toxicity for each individual pathogen varies over a significant range. Accordingly, the significant amount necessary to control a particular pathogen can be determined empirical by in vitro studies of the type described below. Based on such studies an "effective amount" can be determined for a particular target organism.

EXAMPLE 1

Plant Protection Assay of ATCC 53522 Using Alfalfa

The screening procedure disclosed above was repeated as an application of the plant protection assay to test the protective ability of ATCC 53522 with alfalfa. The cultivar of alfalfa used was Iroquois. The fungus used was Pmm. One gram of seeds was soaked in 18M sulfuric acid for ten minutes, washed in 2 l of sterile distilled water, placed in 10 ml of sterile distilled water, and shaken at 28° C. for 24 hours. Thereafter, the seed coats were removed with forceps, and the seedlings were planted in test tubes containing 5 ml of moist vermiculite. Three seedlings were planted in each test tube. After two days, each test tube was inoculated with 0.3 ml of a three day old culture of ATCC 53522 that had been grown in TSB to saturation. Thereafter, each tube was inoculated with $10^3$ zoospores of Pmm. The plants then were incubated at 24° C. with a 12 hour photo period for 7 days, whereupon the plants were evaluated for viability. All of the control seedlings were dead. Most of the seedlings that had been treated with ATCC 53522 had the appearance of normal seedlings that had not been exposed to Pmm.

EXAMPLE 2

Plant Protection Assay of ATCC 53522 with Soybeans

The procedure of Example 1 was repeated with soybeans of the variety McCall substituted for the alfalfa seeds and zoospores of *Phytophthora megasperma* f. sp. *alycinea* substituted for the zoospores of Pmm. Instead of being planted in test tubes, the soybean seeds were planted in 10 ml plastic cones having holes in the bottom, and the cones were placed in a pan of water. The seedlings were examined for protection two weeks after inoculation with the zoospores. Ten out of 10 controlled seedlings were killed by the fungus. All of the seedlings that had been treated with ATCC 53522 survived with healthy, white roots.

EXAMPLE 3

Field Test of ATCC 53522

Alfalfa seeds of the cultivar Iroquois were mixed in a suspension of ATCC 53522 in 1.5% methyl cellulose. The bacteria had been cultured on a TSA plate that had been incubated at 30° C. for three days, by which time the culture had sporulated. The culture then was scraped into 3 ml of the 1.5% methyl cellulose solution to provide the suspension of bacteria. One gram of alfalfa seeds was added to this suspension and was mixed thoroughly therewith. The seed then was spread on sterile petri plates and dried overnight in a laminar flow hood. The coated seeds were planted in circular plots 0.3 m in diameter at Marshfield, Wis. Owing to dry growing conditions, both emergence of plants and evidence of Pmm damping off were poor. Nevertheless, emergence in a control, untreated plot was 18% whereas in the plot planted with bacterium-treated seed, emergence was 30%. An additional plot was planted with seed that had been coated with a fungicide, metalaxyl, a conventional control agent for damping off. In that plot, emergence was 29%. Thus, it is apparent that ATCC 53522 can protect alfalfa in the field as effectively as does metalaxyl. Furthermore, symptoms of root rot became apparent in the control plot having untreated seeds as the growing season proceeded. No symptoms of root rot appeared in the plot planted with the seeds coated with ATCC 53522.

EXAMPLE 4

Plant Protection Assay of ATCC 53522 Toxin

The method of Example 1 was repeated with ATCC 53522 being replaced with a filtrate of a culture of that bacterium. The filtrate was prepared by centrifuging a two day old, saturated broth culture at 10,000 g for ten minutes and then filtering the resulting supernatant twice through 0.45$\mu$ filters. The filtrate was stored at −20° C. before being applied in the plant protection assay identically to the way the bacteria had been applied in the experiment reported as Example 1. The protective effect observed in treated alfalfa seedlings versus untreated seedlings was identical to that reported in Example 1. The filtrate used in this example contained *Bacillus cereus* antibiotic.

EXAMPLE 5

Spontaneous Mutants of ATCC 53522

Spontaneously developing antibiotic resistant mutants of ATCC 53522 were isolated by plating a culture derived from a colony of ATCC 53522 on media containing an antibiotic to which ATCC 53522 normally is sensitive. Several resistant colonies developed. They were each sampled with a sterile toothpick and replated on the antibiotic-containing media. The mutants were then tested in the plant protection assay by the procedure described in Example 1. Five mutants were developed that were resistant to rifampicin. A sixth mutant was developed that was resistant to neomycin. Each of the mutants protected alfalfa plants in the plant protection assay as applied in Example 1 as effectively as did ATCC 53522.

EXAMPLE 6

Induced Mutants of ATCC 53522

A culture of vegetatively growing cells of ATCC 53522 was prepared and diluted to a density of 108 cells/ml. A quantity of this culture was treated by exposure to 1 $\mu$g/ml N-methyl-nitrosoguanidine for thirty minutes at room temperature. The cells then were washed with water and dilution plates were prepared on TSA. The treatment with N-methyl-nitrosoguanidine had killed 99% of the bacteria in the original culture. Thus, the remaining viable bacteria each had a high probability of containing at least one mutation. Of 500 such bacteria derived from independent colonies, 490 were able to protect alfalfa plants against Pmm when tested by the method of Example 1.

EXAMPLE 7

The assay procedure of Example 1 was again used to demonstrate that the plant protection activity resides with the *Bacillus cereus* antibiotic by testing filtrate fraction activity with the natural strain and antibiotic deficient mutants. Strain T30 is such an antibiotic deficient mutant derived from *Bacillus cereus* ATCC 53522. The results of this procedure are demonstrated in Table 1 below.

TABLE 1

Plant Survival

| Treatment | Alfalfa | Tobacco |
|---|---|---|
| None | 0/18 | 0/12 |
| ATCC 53522 | 18/18 | 12/12 |
| ATCC 53522 filtrate | 18/18 | 12/12 |
| ATCC 53522 500–1000 fraction | 18/18 | 12/12 |
| T30 | 0/18 | 2/12 |
| T30 filtrate | 0/18 | 1/12 |
| T30 500–1000 fraction | 0/18 | 0/12 |

This demonstrates that the plant protecting activity is in the *Bacillus cereus* antibiotic independent of the bacteria, and that the activity is absent in antibiotic deficient mutants.

EXAMPLE 8

Isolation of Phage P7

A culture of ATCC 53522 was grown in trypic soy broth with vigorous agitation. During the log-phase growth phase of the bacteria, mitomycin C was added to the media to a final concentration of 1 $\mu$g/ml. The bacteria in culture lysed 8 to 9 hours after the addition of the mitomycin C. Phage particles were isolated from the remaining culture by plating aliquots of the culture on a lawn of ATCC 53522 grown in soft agar (0.4%). Individual plaques were then picked and replated again into a similar subculture. The P7 phage has been propagated by plating sufficient lysate on a culture of a ATCC 53522 on a soft agar overlay to result in clearing of the overlay. The overlay has been typically removed from the plate, the agar removed by centrifugation, and the supernatant stored for future use. Later, the supernatant was reinoculated onto culture to continue to propagate and isolate additional phage P7. Samples of the phage P7 have been deposited with the ATCC as Accession No. 75237.

EXAMPLE 9

Isolation of Other Biocontrol Bacteria

Additional populations of *Bacillus cereus* were recovered from soil or from field-grown soybeans and from alfalfa, soybeans and snapbeans plants grown in field soils in the growth chamber. The samples were dilution plated by sonicated samples of soil, seeds, cotyledons, radicles or 1 to 2 cm root segments taken from 0–1, 0–2, 2–3, 4–5, or 9–10 cm below the crown, or from the last cm of the root. For this purpose, the crown was defined as the part of the plant at the soil-air interface which was marked on each plant as it was removed from the soil. Plant materials placed at either 5 or 10 ml of sterile distilled water, which was then sonicated for 15 seconds at 20% output with a 250 W Vibra-cell sonicator (Sonics and Materials) and then serially diluted in sterile distilled water. Aliquots (0.1 ml) of the dilutions were then plated onto a semi-selective medium. The semi-selective medium (Min IC) medium was used because few non-Bacillus bacteria will grow on it, thereby semi-selecting for the detection of *Bacillus cereus*. The Min IC medium contained, per liter, 2.0 g of $(NH_4)_2SO_4$, 6.0 g of $KH_2PO_4$, 14.0 g of $K_2HPO_4$, 0.2 g of $MgSO_4$-$7H_2O$, 0.25 mg of $MnSO_4$—$H_2O$, 1.0 g of trisodium citrate-2 $H_2O$, 0.1 g of thiamine hydrochloride, 2.0 g of L-glutamic acid, and 5.0 g of acid-hydrolyzed casein (Sigma). After autoclaving, 10 ml of a sterile 50% (wt/vol) glucose solution and 10 ml of sterile $FeCl_3$-$6H_2O$ (4.0 mg/ml) were added. The Min IC medium was also inoculated with 12.5 micrograms/ml polymyxin B-sulfate, 50 $\mu$g/ml ampicillin, and 100 $\mu$g/ml cycloheximide. The *B. cereus* isolates that were collected from the field were screened on a semi-selective media. Colonies of *B. cereus* were identified by their distinctive colony morphology, i.e., large, flat, wrinkled, cream or orange colored colonies, on the semi-selective medium.

EXAMPLE 10

Screening of Putative Biocontrol Agents

The biocontrol agents isolated in this fashion were then subjected to a selection criteria based on the use of three assays which have been found to have strong correlations with each other, and which are capable of identifying *Bacillus cereus* strains which are capable of biocontrol activity and which produce the zwittermicin A toxin. One assay is based on the susceptibility of the candidate strain to infection by the P7 phage. The second test is based on a laboratory biocontrol study using *Erwinia herbicola*. The third study is an actual stain assaying for the production of the zwittermicin A toxin itself. All of these assays correlate well, although not perfectly. So far, however, every strain except one found to be susceptible to P7 has tested positive for Erwinia inhibition and has stained for antibiotic production. The results of these assays, done collectively or singly, may be verified by biocontrol studies on actual plants.

The phage sensitivity selection was done using the following protocol. High titer preparations (in excess of $10^9$ pfu/ml) of phage P7 were prepared either from infected broth cultures or from top agar overlays of *Bacillus cereus* ATCC 53522 as described in the prior example. The cells were removed by centrifugation and the supernatants were filtered (0.2 micron or 0.45 micron filters). The phage preparations were titered and stored in a refrigerator. Separately, cultures of the candidate organisms were grown on 50% trypsin soy agar (TSA). The growth is scraped from the culture plate, suspended in a small volume of 50% trypsin soy broth (TSB), and added to three milliliters of molten 50% TS top agar (0.4% agar) and spread on a plate of 50% TSA. Drops of the high titer phage stock, approximately 10 microliter in size, were placed on the plate. The plates were incubated overnight at 28° C. If the drop of phage introduced into the culture caused a clear zone, the strain was scored as sensitive to the phage.

The laboratory biocontrol assay for *Erwinia herbicola* inhibition was conducted as follows: The Erwinia culture was grown in 50% TSB with shaking, over night, at 28° C. The Erwinia cells were allowed to settle to the bottom of the tube and the stock of Erwinia was stored in the refrigerator, sometimes for as much as two weeks. The candidate *B. cereus* strain to be tested was grown in 50% TSB, with shaking, at 28° C., for two to three days. Fifteen microliters from the top of the Erwinia stock tube, taken without shaking the tube, was placed in 1 milliliter of sterile water. Eighty-five microliters of the Erwinia dilution was then spread on water agar or 25% tryptic soy agar in a plate. Four holes were cut in the plate with a sterile cork borer. Approximately 100 microliters of the candidate *B. cereus* test culture was added to each of the holes cut in the plate. The zones of inhibition of Erwinia growth around the *B. cereus* cultures were scored in two to three days. Candidates were scored as positive if a zone of inhibition appeared.

To assay for the production of the zwittermicin A toxin, cultures of the candidate *B. cereus* cultures were maintained under conditions described above. The cultures were fully sporulated and centrifuged to remove spores. The supernatant was applied to a CM Sephadex cation exchange column in the ammonia form. The column was then washed with buffer (6 mil 10 mM N,N bis (2-hydroxyethyl) 2-amino ethane sulfonic acid, pH 7.0). The bound toxin, if present, was eluted with 10 mM 3-cyclohexylamino propane sulfonic acid, pH 10.4. Fractions were collected, dried in a rotary evaporator and resuspended in water. Resuspended material was spotted onto filter paper and subjected to preparative high voltage paper electrophoresis at pH 1.7 and 300 volts for 15 minutes. Filter paper that had been subjected to electrophoresis was stained by dipping in a solution containing 0.25% ninhydrin in acetone. The plates of paper were dried and heated at 110° C. until spots were visible. The occurrence of ninhydrin staining spots verified production of the antibiotic.

The following Table 2 summarizes the results of assaying the isolated strains. The results demonstrate that the three laboratory tests, P7 susceptibility, Erwinia inhibition, and antibiotic detection correlate nicely with each other and with biocontrol activity. While some strains may fail one of the tests and still have biocontrol capability, so far each strain that has passed one or more assay has exhibited biocontrol activity. Hence these assays, singly or collectively, provide useful laboratory tools to select new biocontrol strains.

TABLE 2

Correlation between Phase Sensitivity, Antibiotic Production and Biocontrol Activity for *B. cereus* isolates

| Strain | P7 Assay | Erwinia Assay | Antibiotic detected | Biocontrol Activity |
|---|---|---|---|---|
| ATCC 53522 | + | + | + | + |
| Laboratory Strains (7 strains) | – | – | – | nt |
| Soil Isolates | | | | |
| 1 | + | + | + | + |
| 3 other strains | – | – | nt | nt |
| 86 strains | – | nt | nt | nt |
| Soybean Root Isolates | | | | |
| 1 | + | + | + | + |
| 5 other strains | – | – | nt | nt |
| 39 other strains | – | nt | nt | nt |
| Alfalfa Root Isolates | | | | |
| 1 | + | + | + | + |
| 2 | + | + | + | + |
| 3 | + | + | + | + |
| 8 strains | – | + | + | + |
| 1 strain | – | – | – | + |
| 11 strains | – | – | – | – |
| 154 strains | – | – | nt | nt | nt = not tested

EXAMPLE 11

A *B. cereus* ATCC 53522 cultures were grown in half-strength trypticase soy broth (TSB). Then 1 liter, three-day old fully sporulated cultures were centrifuged to remove spores and the culture supernatant were adjusted to pH 7.0 with 2.0 M $NaH_2PO_4$ and then applied to a column (2.2 cm×30.0 cm) containing Amberlite IRC-50 (Sigma). The column was washed with 5.0 mM $NH_4HPO_4/NH_3$ pH 7.0 and eluted with 1.0 M $NH_3$ pH 11.2. The material in approximately 30 mls was collected from the-column after the pH was raised above 10, dried in an evaporator, and quantified.

The active fractions were then purified by high voltage electrophoresis (HVPE) at pH 9.2. From the electrophoretograms, two spots were identified with the two antibiotics, zwittermicin A and antibiotic B. The spot for zwittermicin A had a relative mobility ($R_f$) of 0.30 compared to Orange G. The spot for antibiotic B had an $R_f$ of 0.032. These spots were eluted and subjected to HVPE at pH 1.7, at which the antibiotics exhibited mobilities similar to a di-cation ($R_f$=–1.042 for zwittermicin A and $R_f$=–0.909 for antibiotic B).

Separately, a panel of bacterial and fungal pathogenic strains were collected for use in an assay with purified zwittermicin A and antibiotic B to test antibiotic activity. The bacterial strains were all tested in Muller-Hinton (MH) broth (Sigma) at pH 7.3 and MH broth buffered with 3-(n-morpholino) propanesulfonic acid (MOPs) to pH 8.0. The susceptibility testing of the Rhizobium and Lactobacillus strains were conducted in L-broth (Maniatis, 1982). Other strains requiring special treatment were the Rhodosprillum which was grown in MH broth to which 1 μg/ml of biotin was added, and the Clostridium which was grown in MH broth to which was added 20 μg/ml of sucrose.

The susceptibility testing of the fungal strains described below as conducted on potato dextrose agar (PDA, at pH 5.6 and PDA buffered with MOPs to pH 7.0.

For the bacterial susceptibility testing, the minimum inhibitory concentration (MICs) were determined by a broth dilution procedure. The inocula were prepared from fresh broth cultures and diluted to provide inoculum concentrations of approximately $5\times10^5$ CFU/ml. Antibiotics were added in two-fold dilutions, ranging from 50 μg/ml to 400 μg/ml and each test tube contained 1 ml. The cultures were incubated at 28° C. with shaking for 24 h, (48 h for *Lactobacillus acidophilus, Streptomyces griseus, Rhizobium meliloti, Rhizobium tropici, Rhodobacter sphaeroides*, and *Rodosprillum rubrum*). *Clostridium pasteurianum* was tested under anaerobic conditions by overlaying the culture with 3 ml of sterile mineral oil and then growing the culture for 4 days at room temperature. MICs were interpreted as the lowest antibiotic concentration that prevented visible growth. Bacteria with MICs of 50 μg/ml for zwittermicin A were retested at 0 to 50 μg/ml antibiotic in 10 μg increments. Minimal bactericidal concentrations (MBCs) were determined for each bacterial strain by spreading 0.1 ml from each test culture without visible growth onto Muller-Hinton agar (Sigma Chemicals) plates. The plates were scored for bacterial growth after incubation at 28° C. for 24 to 48 h.

The zoosporic fungi were tested as follows: Zoospores of *Aphanomyces euteiches* ($2\times10^4$), *Phytophthora medicaginis* ($5\times10^4$), *Pythium aphanidermatum* ($1\times10^3$) and *Pythium torulosum* ($1\times10^3$) were spread onto PDA plates. A well was cut into the center of the agar with a sterilized cork borer. Purified antibiotic was pipetted into the well and the plates were incubated at room temperature for 48 h. Zones of inhibition were measured from the well to visible growth. MICs in this assay were the lowest antibiotic concentration that resulted in a zone of inhibition. *Candida utilus, Saccharomyes cerevisiae* and *Ustilago maydis* were tested by the same procedure and approximately $1\times10^4$ CFUs were spread on the PDA plates. *Venturia inaequalis* was tested by mixing $2\times10^5$ conidia into 25 ml of 50% PDA. The agar was vortexed briefly and then poured into a petri plate. A well was cut into the plate for the placement of antibiotic. The other fungi were tested for antibiotic susceptibility as follows: PDA plates were incubated with a plug of mycelia in the center of the plate. A well was cut into the agar 5 to 10 mm from the plug. Purified antibiotic (200) μg, was placed in the well and the plates were incubated at room temperature. Because of the variable growth rates of the test fungi, the plates were scored for growth after 2 to 6 days.

The data from the in vitro testing of antibiotic zwittermicin A and antibiotic B against bacteria is listed on Table 3 below while the results obtained from the testing against fungal pathogens is listed on Table 4 below. Also shown below, in Table 5, is an experiment conducted in which the combined activity of zwittermicin A and antibiotic B was evaluated against *E. coli*, at various combinations of each of the two antibiotics.

TABLE 3

In vitro activities of zwittermicin A and antibiotic B against bacteria

| Bacteria tested | MIC (µg/ml)[a] | |
|---|---|---|
| | ZmA | Ant B |
| *Agrobacterium tumefaciens* A759 | 40 | >400 |
| *Bacillus cereus* 569 | >400 | >400 |
| *Bacillus cereus* UW85 | >400 | >400 |
| *Bacillus cereus* BAR145 | >400 | >400 |
| *Bacillus subtilis* 168 | >400 | >400 |
| *Bacillus thuringiensis* 4A9 | >400 | >400 |
| *Bacillus thuringiensis* 4D6 | >400 | >400 |
| *Bradyrhizobium japonicum* USDA 110 | 100 | >400 |
| *Clostridium pasteurianum* 5002 | >400 | >400 |
| *Cytophaga johnsonae* 9408 | >400 | 300 |
| *Escherichia coli* K37 | 100 | >400 |
| *Erwinia carotovora* 8064 | 40 | >400 |
| *Erwinia herbicola* IRQ | >400 | >400 |
| *Erwinia herbicola* LS005 | 50 | 400 |
| *Klebsiella pneumoniae* 8030 | 200 | >400 |
| *Lactobacillus acidophilus* 4003 | 100 | >400 |
| *Pseudomonas aeruginosa* 9020 | >400 | >400 |
| *Pseudomonas fluorescens* 9023 | >400 | >400 |
| *Rhizobium tropici* CIAT 899 | 100 | >400 |
| *Rhizobium meliloti* 1021 | 50 | >400 |
| *Rhodobacter sphaeroides* 9502 | 50 | 400 |
| *Rhodospirillum rubrum* 9405 | 50 | >400 |
| *Salmonella typhimurium* LT2 | 100 | >400 |
| *Staphylococcus aureus* 3001 | 200 | 400 |
| *Streptomyces griseus* 6501 | 400 | >400 |
| *Vibrio cholerae* F115A | 400 | >400 |

TABLE 4

In vitro activities of zwittermicin A and antibiotic B against various fungi

| Fungi tested | Disease incited | Inhibition[a] | |
|---|---|---|---|
| | | ZmA | Ant B |
| *Alternaria alternata* | Leaf blight on beet | + | +/− |
| *Alternaria tagetica* | Leaf and petal blight | + | +/− |
| *Aphanomyces euteiches* WI-98 | Seedling blight of alfalfa | + | + |
| *Aspergillus flavus* | Non-pathogenic | − | − |
| *Botrytis cinerea* | Molds and rots of stored fruits and vegetables | + | − |
| *Candida utilus* | Non-pathogenic | + | − |
| *Colletotrichum phomoides* | Anthracnose of tomato | +/− | − |
| *Colletotrichum trifolii* SMM | Anthracnose of alfalfa | + | − |
| *Cytospora cineta* | Branch canker of fruit trees | + | − |
| *Drechslera poae* | Leaf spot/foot rot of grasses | + | +/− |
| *Epicoccum nigrum* | Leaf spot of magnolia | + | − |
| *Fusarium oxysporum* f. sp. *lycopersici* | Vascular wilt of tomato | − | − |
| *Fusarium sporotrichioides* | Blight of barley and sunflower | + | +/− |
| *Fusarium solani* | Root rot of bean | + | − |

TABLE 4-continued

In vitro activities of zwittermicin A and antibiotic B against various fungi

| Fungi tested | Disease incited | Inhibition[a] | |
|---|---|---|---|
| | | ZmA | Ant B |
| *Helminthosporium carbonum* | Leaf spot and ear rot of corn | + | +/− |
| *Helminthosporium sativum* | Foot rot of grasses | + | +/− |
| *Ophiostoma ulmi* | Dutch elm disease | +/− | − |
| *Phoma obscurans* | Leaf spot of strawberry | + | +/− |
| *Phytophthora medicaginis* | Root rot of alfalfa | + | + |
| *Pythium torulosum* | Damping-off of tobacco | + | + |
| *Pythium aphanidermatum* | Root rot of vegetables | + | + |
| *Rhizoctonia solani* (AG1, AG4) | Root rot of fruits/vegetables | + | − |
| *Saccharomyces cerevisiae* | Non-pathogenic | − | − |
| *Sclerotinia homoecarpa* | Dollar spot of turf | − | − |
| *Sclerotinia sclerotiorum* | Rots of most crops | + | − |
| *Typhula incarnata* | Snowmold of turf/grasses | − | − |
| *Ustilago maydis* | Smut of corn | + | + |
| *Venturia inaequalis* | Scab of apple | + | + |
| *Verticillium dahliae* | Wilt of potato | +/− | − |
| *Verticillium albo-atrum* | Wilt of alfalfa | +/− | − |

TABLE 5

Combined activity of zwittermicin A and antibiotic B against *E. coli*

| | | Zwittermicin A (µg/ml) | | | | | | |
|---|---|---|---|---|---|---|---|---|
| | | 0 | 10 | 15 | 20 | 25 | 30 | 40 |
| Antibiotic B (µg/ml) | 0 | +++ | + | + | + | + | + | − |
| | 50 | +++ | + | + | + | − | − | − |
| | 100 | ++ | + | + | − | − | − | − |
| | 200 | ++ | − | − | − | − | − | − |
| | 300 | ++ | − | − | − | − | − | − |
| | 400 | − | − | − | − | − | − | − |

Growth of *E. coli* strain K37 ranged from saturated cultures (+++) to no visible growth (−).

As the above data demonstrates, the antibiotics have broad spectrum activity against a variety of fungal pathogens and also have significant activity against many bacterial pathogens. In addition, from the *E. coli* study, it appears that the action of the antibiotics is synergistic and that they act in concert to achieve levels of inhibition that neither would achieve alone.

What is claimed is:

1. A composition of matter comprising a compound having the following formula:

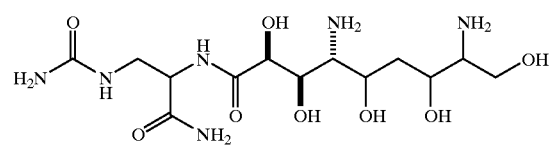

and an agriculturally or pharmaceutically acceptable carrier; the composition free of *Bacillus cereus* bacteria.

* * * * *

UNITED STATES PATENT AND TRADEMARK OFFICE
CERTIFICATE OF CORRECTION

PATENT NO. : 6,034,124
DATED : March 7, 2000
INVENTOR(S) : Jo Handelsman, Laura Silo-Suh, Jon Clardy, Haiyin He It is certified that error appears in the above-identified patent and that said Letters Patent is hereby corrected as shown below:

On the title page of the patent, Item [73] Assignee, following "Wis." insert -- and Cornell Research Foundation, Inc., of Ithaca, N.Y.--.

Signed and Sealed this

First Day of August, 2000

*Attest:*

Q. TODD DICKINSON

*Attesting Officer*  *Director of Patents and Trademarks*